(12) United States Patent
Estrada et al.

(10) Patent No.: US 8,132,463 B2
(45) Date of Patent: Mar. 13, 2012

(54) METHOD AND APPARATUS FOR DETECTING VOIDS IN A PIPE

(75) Inventors: Herbert Estrada, Annapolis, MD (US);
Ernest Hauser, Pittsburgh, PA (US);
Matthew Mihalcin, Pittsburgh, PA (US);
Donald R. Augenstein, Pittsburgh, PA (US)

(73) Assignee: Cameron International Corporation, Houston, TX (US)

( * ) Notice: Subject to any disclaimer, the term of this patent is extended or adjusted under 35 U.S.C. 154(b) by 513 days.

(21) Appl. No.: 12/316,951

(22) Filed: Dec. 18, 2008

(65) Prior Publication Data

US 2010/0154548 A1    Jun. 24, 2010

(51) Int. Cl.
*G01N 29/02* (2006.01)
(52) U.S. Cl. .......... 73/641; 73/599; 73/600; 73/602
(58) Field of Classification Search ............ 73/641, 73/40.5 A, 54.07, 290 R, 861.354, 861.356, 73/865.8, 599, 600, 602
See application file for complete search history.

(56) References Cited

U.S. PATENT DOCUMENTS

| 4,542,644 A * | 9/1985 | Claytor et al. ............ 73/61.75 |
| 4,722,224 A * | 2/1988 | Scheller et al. .............. 73/599 |
| 5,587,534 A * | 12/1996 | McColskey et al. .......... 73/623 |
| 7,096,135 B2 * | 8/2006 | Ao et al. ................. 702/79 |
| 7,188,534 B2 * | 3/2007 | Tombs et al. ........... 73/861.356 |
| 7,207,229 B2 * | 4/2007 | Mattar et al. ........... 73/861.354 |
| 7,226,203 B2 * | 6/2007 | Rondeau et al. ............... 366/8 |
| 7,698,954 B2 * | 4/2010 | Tombs et al. ........... 73/861.356 |
| 2010/0305870 A1 * | 12/2010 | Camilli et al. ............... 702/24 |

OTHER PUBLICATIONS

A simple system for detecting and measuring gas voids in safety-related fluid systems, Estrada et al., Nov. 2009.*

* cited by examiner

*Primary Examiner* — J M Saint Surin
(74) *Attorney, Agent, or Firm* — Ansel M. Schwartz

(57) ABSTRACT

An apparatus for detecting and measuring gas voids in a pipe with a fluid includes a first ultrasonic transducer externally disposed on the pipe. The apparatus includes a second ultrasonic transducer externally disposed on the pipe. The apparatus includes a multiplexer, transmitter, receiver, controller and processor in communication with the first transducer and the second transducer which in combination identify a void in the pipe from ultrasonic measurements of properties of the fluid in the pipe. A method for detecting and measuring gas voids in a pipe with a fluid includes the steps of measuring properties of the fluid internal to the pipe with transmissions of ultrasonic energy from transducers externally disposed on the pipe. There is the step of identifying a void in the pipe from the properties of the fluid internal to the pipe using signals processed by processor.

23 Claims, 7 Drawing Sheets

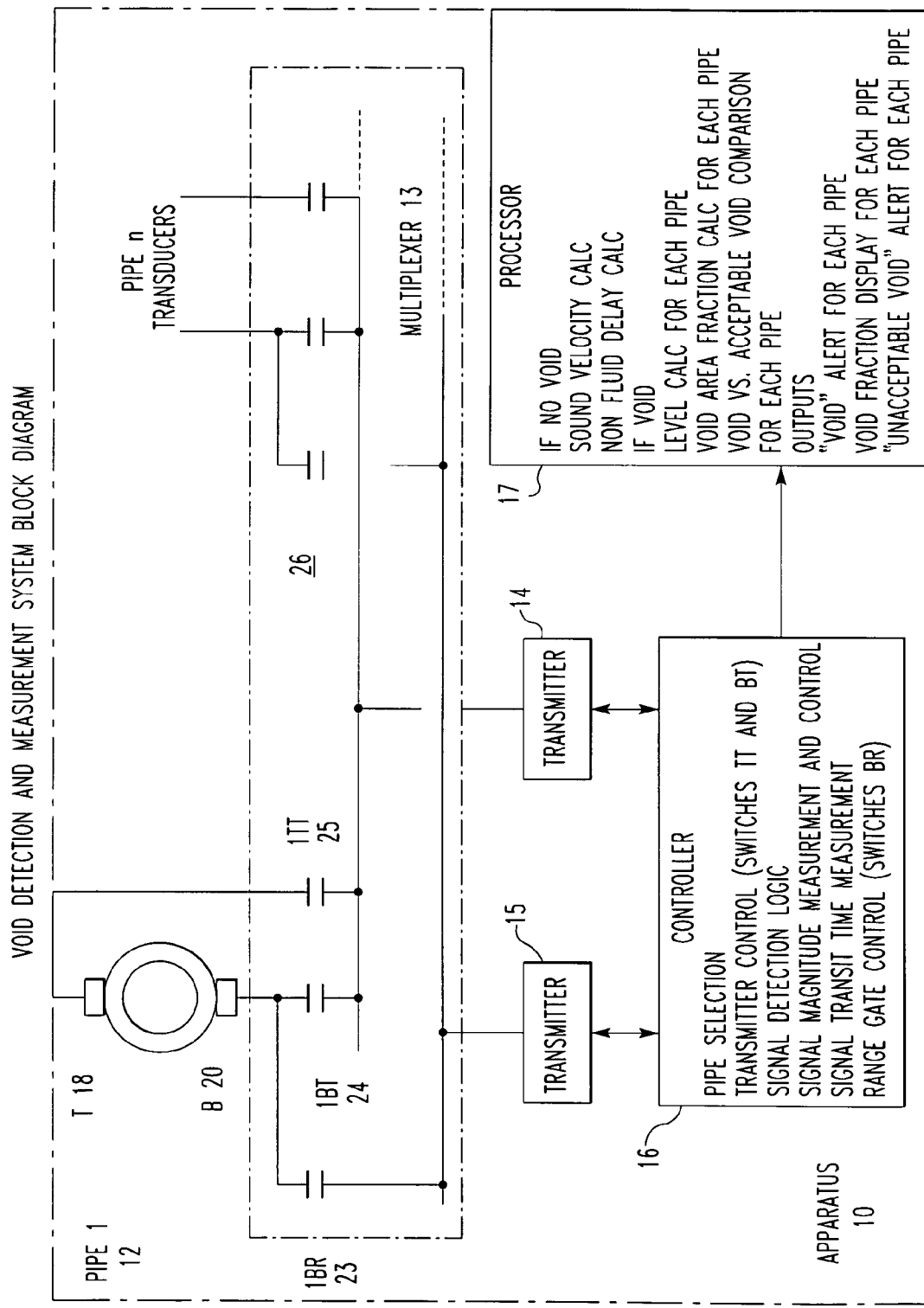

METHOD AND APPARATUS FOR DETECTING VOIDS IN A PIPE

FIELD OF THE INVENTION

The present invention is related to the detection and measurement of gas voids in a pipe with a fluid. (As used herein, references to the "present invention" or "invention" relate to exemplary embodiments and not necessarily to every embodiment encompassed by the appended claims.) More specifically, the present invention is related to the detection and measurement of gas voids in a pipe with a fluid using ultrasonic transmissions that do not require the modification or penetration of the pipe to which the transmissions are applied.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Over the past 20 years, there have a number of instances where nuclear power plant operators have discovered gas voids—typically, air but occasionally other gases such as undissolved hydrogen—in fluid systems that are important to reactor safety. Typical fluid systems can be emergency core cooling systems, decay heat removal systems, and containment spray systems, to name a few. The amount of gas voids has, in some cases, been sufficient to call into question the operability of the fluid systems, if and when they are needed. In fact, initiation of a fluid system with gas voids present may lead to gas binding of its pumps, or destructive water hammer, for example. The sources of the gas have been various and are not readily controlled, thus detection of these voids is pertinent to various industries.

The need for nuclear plant licensees to manage gas accumulation has been formally identified in Nuclear Regulatory Commission generic letter 2008-01. The letter points out a need for continuous monitoring to detect and quantify gas voids in these systems, to ensure their availability in accordance with design basis requirements. The letter further notes that periodic functional tests of the critical systems will not provide the required assurance of operability; if a test finds a system's functionality questionable because of gas accumulation, the question of how long its operability has been compromised is unanswered.

The system disclosed herein addresses these issues definitively. It provides the ability to detect the onset of void formation in any one of multiple pipes in multiple systems on a continuous basis and, following void formation, the ability to quantify the amount of these voids, again continuously.

BRIEF SUMMARY OF THE INVENTION

The present invention pertains to the detection and measurement of gas voids in a pipe with fluid. The measurement is performed using ultrasonic transducers that are disposed externally on the pipe. The capability to transmit and receive ultrasonic signals along geometrically defined paths reveals the presence or absence of voids in the pipe, and the measurement of transit times of these ultrasonic signals defines the characteristics of the void.

BRIEF DESCRIPTION OF THE SEVERAL VIEWS OF THE DRAWING

In the accompanying drawings, the preferred embodiment of the invention and preferred methods of practicing the invention are illustrated in which:

FIG. 1 is a block diagram of an apparatus of one of two configurations (also referred to as modes of operation) disclosed for the present invention.

DETAILED DESCRIPTION OF THE INVENTION

Figure 3:
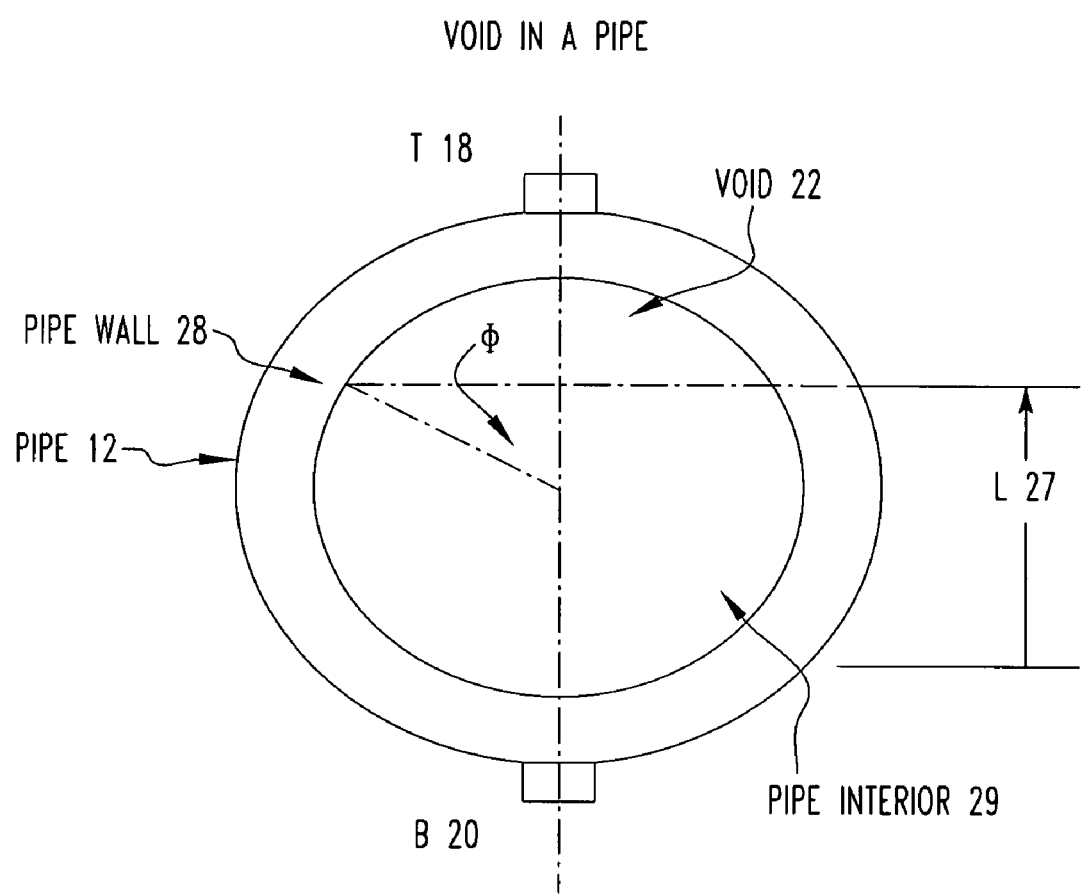
FIG. 3 is a representation of a void in a pipe.

Referring now to the drawings wherein like reference numerals refer to similar or identical parts throughout the several views, and more specifically to FIGS. 1 and 3 thereof, there is shown an apparatus 10 for detecting and measuring gas voids in a pipe 12 with a fluid. The apparatus 10 comprises a first ultrasonic transducer externally disposed on the pipe 12. The apparatus 10 comprises a second ultrasonic transducer externally disposed on the pipe 12. The apparatus 10 can comprise a multiplexer 13, transmitter 14, receiver 15, controller 16 and processor 17 in communication with the first transducer and the second transducer which identifies a void in the pipe 12 from ultrasonic measurements of properties of the fluid in the pipe 12. All of these components can be connected to electronic memory.

The first ultrasonic transducer can be disposed externally on the top of the pipe 12, and the second ultrasonic transducer can be disposed externally on the bottom of the pipe 12 essentially below the first transducer. There can be a controller 16; a multiplexer 13; a transmitter 14 and a receiver 15 in communication via the multiplexer 13 with the first and second transducers which causes the first and second transducers to produce ultrasonic transmissions to occur sequentially as follows:

A transmission from the first transducer to the second transducer; if the transmission is received by second transducer as sensed by the receiver 15 and the controller 16, there is no void present; if the transmission by the first transducer is not received by second transducer, a void is present.

A transmission from the second transducer that is reflected either off the pipe's 12 upper wall, if no void is present or off the liquid surface if a void is present.

In the first configuration (or mode) of the disclosed invention, if the transmission from the first transducer is received by the second transducer, transit times from this transmission and from a transmission from the second transducer to itself via a reflection can be converted by the processor 17 into an approximate measurement of fluid sound velocity. In the second configuration (or mode) of the disclosed invention, if the transmission from the first transducer is received by the second transducer, transit times from the first, second and additional transmissions are employed to determine sound velocity without approximations. For both disclosed configurations, if the transmission from the first transducer is not received by the second transducer, a transit time of the transmission from the second transducer to itself can be converted by the processor 17 into a liquid-height measurement.

For both disclosed configurations, the conversion to height by the processor 17 can be made using a fluid sound velocity measurement associated with the last transmission from the first transducer for which the last transmission was received by the second transducer.

The processor 17 can determine what fraction of the pipe 12 is filled with gas. The signal from the first transducer can follow a diametric path through the pipe wall 24, the interior of the pipe 12 and the pipe wall 24 to the second transducer if there is no void. The multiplexer 13, transmitter 14, receiver 15, controller 16 and processor 17 can process transmissions to detect and measure voids from additional transducers disposed on other pipes. The processor 17 can issue an alert for the pipe 12 when a threshold associated with a void in the pipe 12 is reached. A transmission from the second transducer can follow and retrace a diametric path through the pipe 12 and the interior of the pipe 12 if there is no void, and a path that lies along the diameter but is a fraction thereof if there is a void.

The present invention pertains to a method for detecting and measuring gas voids in a pipe 12 with a fluid. The method comprises the steps of measuring properties of the fluid internal to the pipe 12 with transmissions of ultrasonic energy from transducers externally disposed on the pipe 12. There is the step of identifying a void in the pipe 12 from the properties of the fluid internal to the pipe 12 using signals processed by processor 17. The steps can be performed on one or more tangible media that includes code for performing the appropriate steps.

There can be the step of causing with a multiplexer 13 and a controller 16 transmissions from a first ultrasonic transducer disposed externally on the top of the pipe 12 and a second ultrasonic transducer disposed externally on the bottom of the pipe 12 essentially below the first transducer. In both configurations of the disclosed invention, the first and second transducers produce ultrasonic transmissions that occur sequentially as follows:

A transmission from the first transducer to the second transducer; if the transmission is received by second transducer as sensed by the receiver 15 and the controller 16, there is no void present; if the transmission by the first transducer is not received by second transducer, a void is present.

A transmission from the second transducer that is reflected from either the pipe's 12 upper wall if no void is present, or the liquid surface if a void is present.

In the first configuration of the disclosed invention (FIG. 1), if the transmission from the first transducer is received by the second transducer, there can be a step of converting transit times from this transmission and from a transmission from the second transducer to itself via a reflection by a processor 17 into a fluid sound velocity measurement. There can also be the step of converting these transit time measurements into an approximate measurement of the non fluid delays in the transmission from the second transducer to itself. If the transmission from the first transducer is not received by the second transducer, there can be step of converting a transit time of the transmission from the second transducer to itself by the processor 17 into a liquid height measurement. The step of converting to height by the processor 17 can include the step of converting to height by the processor 17 using a fluid sound velocity measurement and non fluid delays associated with the last transmission from the first transducer for which the last transmission was received by the second transducer.

Figure 5:
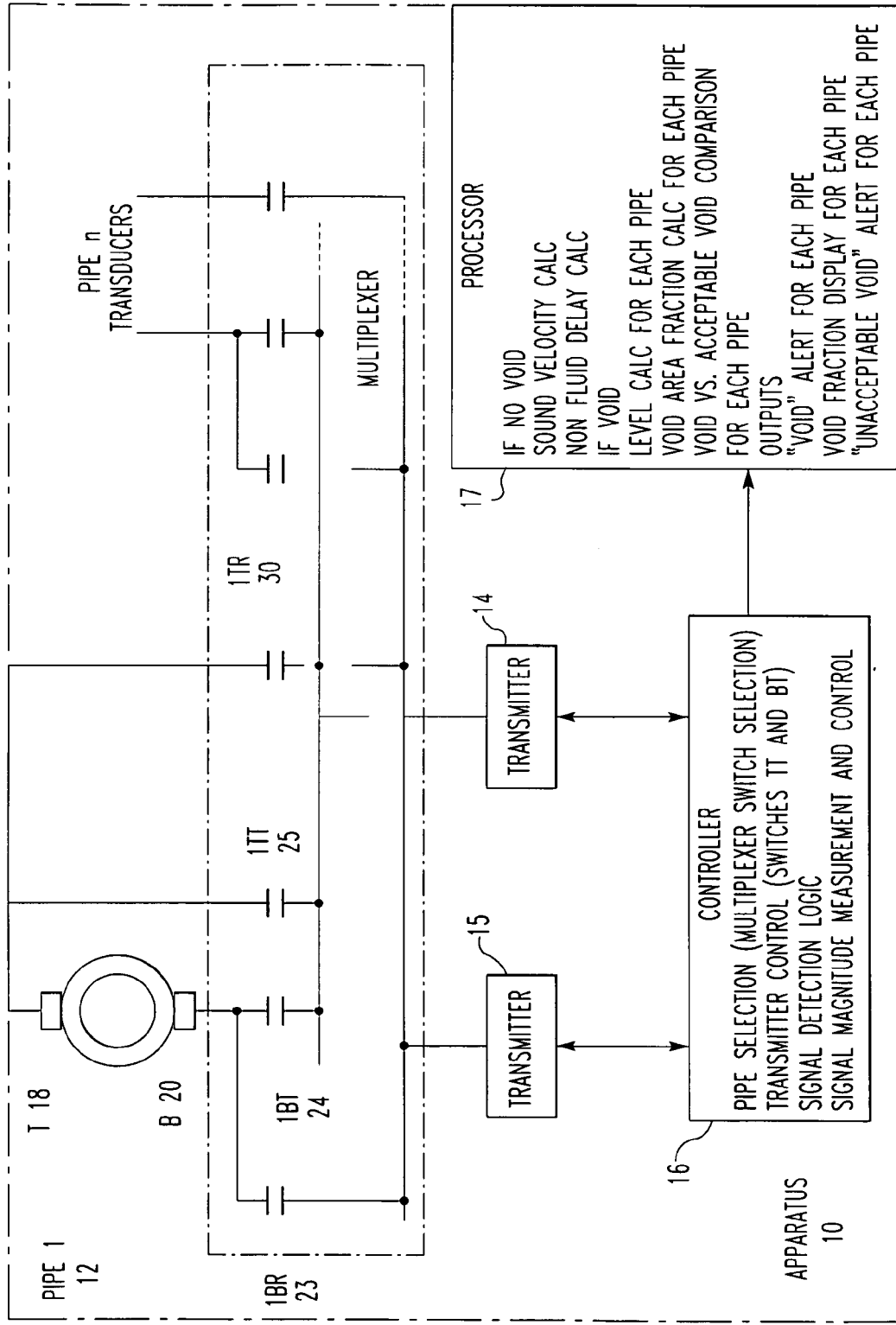
FIG. 5 is a block diagram of the second of the two configurations (or modes) disclosed for the present invention.

The second configuration of the invention disclosed herein (FIG. 5) employs two additional transmissions when the pipe is full. If the transmission from the top transducer 18 is received by the bottom transducer 20, the transit time for this transmission and the transit time from the bottom transducer 20 to itself are measured, as in the first configuration. However, in the second configuration, two additional transmissions are employed when the pipe is full: a transmission from the bottom transducer 20 to the top transducer 18 and a transmission from the top transducer 18 to itself via a reflection from the bottom wall of the pipe. To accomplish these transmissions an additional switch contact, 1TR 30 in the multiplexer 13 of FIG. 5 is necessary. The transit times for these additional transmissions, in combination with the transit times from the first and second transmissions allows the computation by the processor 17 of fluid sound velocity and the non fluid delays without approximation.

For the second disclosed configuration, if the first transmission, from the top transducer toward the bottom transducer, is not received by the bottom transducer, the operation reverts to that of the first configuration: The transit time for the transmission from the bottom transducer to itself is converted to a liquid height, and transmission from the top transducer to itself and the transmission from the bottom transducer to the top transducer are discontinued.

For both disclosed configurations, there can be the step of determining with the processor 17 what fraction of the pipe 12 is filled with gas. The signal from the first transducer can follow a diametric path through the pipe wall 24, the interior of the pipe 12 and the pipe wall 24 to the second transducer if there is no void. There can be the step of processing with the multiplexer 13, transmitter 14, receiver 15, controller 16 and a processor 17 transmissions to detect and measure voids from additional transducers disposed on other pipes. There can be the step of issuing an alert by the processor 17 when a threshold associated with a void in the pipe 12 is reached. A transmission from the second transducer can follow and retrace a diametric path through the pipe 12 and the interior of the pipe 12 if there is no void, and a path that lies along the diameter but is a fraction thereof if there is a void.

Figure 2A:
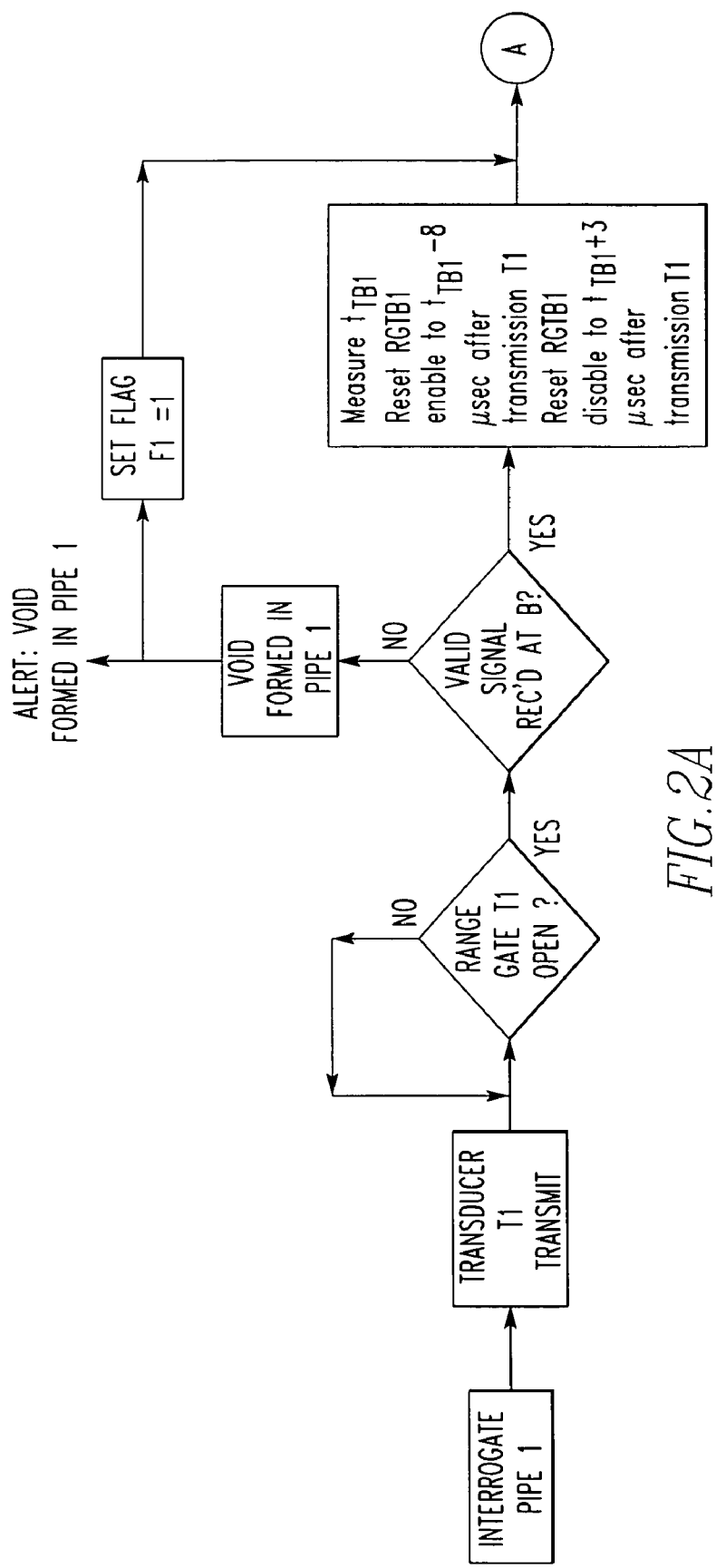
FIG. 2a is a flowchart regarding the operation of the present invention.
Figure 2B:
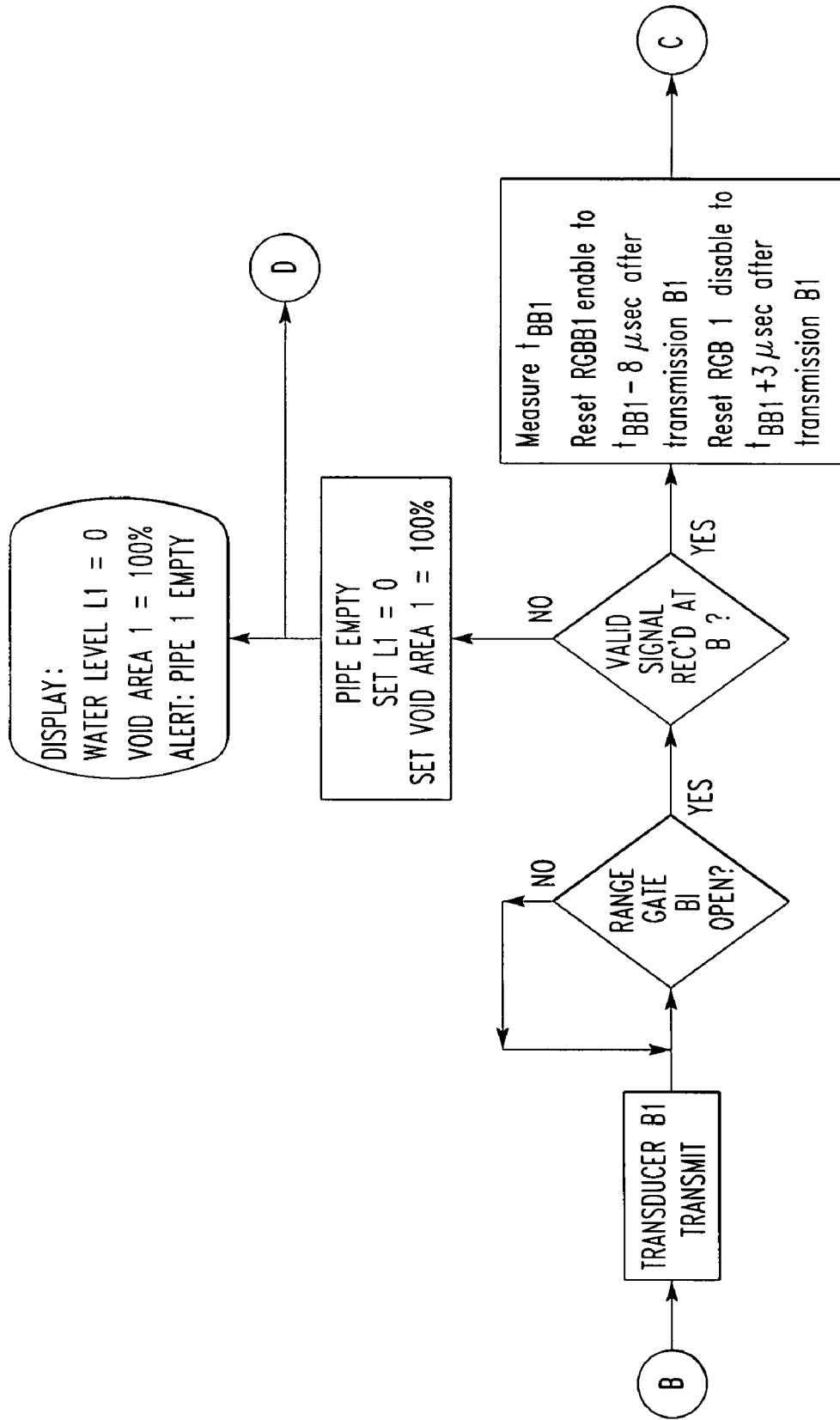
FIG. 2b is a flowchart regarding the operation of the present invention.
Figure 2C:
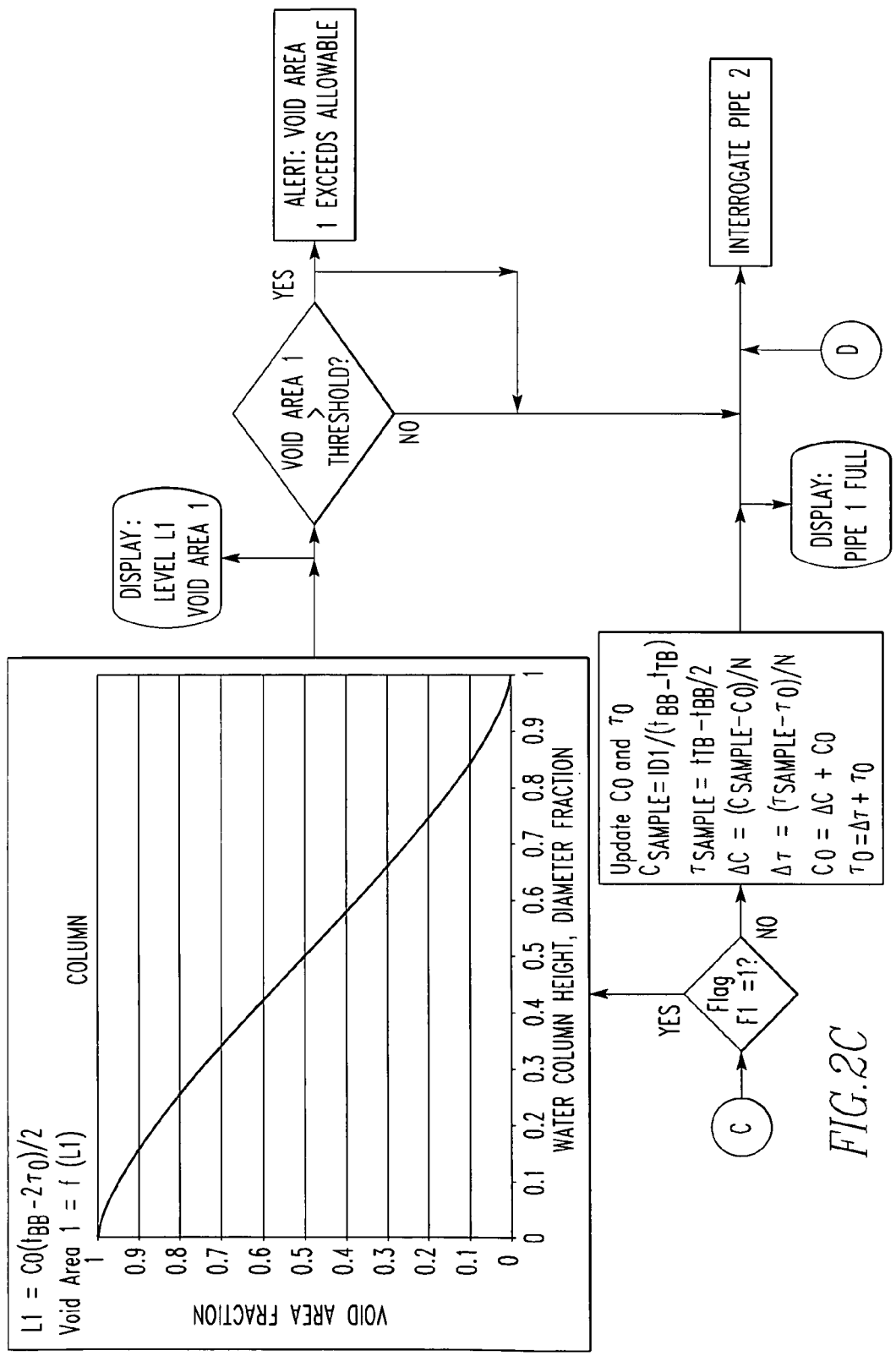
FIG. 2c is a flowchart regarding the operation of the present invention.

In the operation of the invention, and referring to FIG. 1, transducer T and transducer B are ultrasonic transducers affixed to the exterior of a circular pipe 12 normally filled with liquid water, but with the potential for containing voids. As shown in FIG. 1, transducer T is fastened to the top of pipe 12; transducer B is fastened to the bottom. A couplant material, suitable for transmitting ultrasound between transducer and pipe 12, and vice versa, is applied in the interface between each transducer and the exterior pipe wall 24. The transducers are nominally identical in diameter and natural frequency. In the first operational mode of the proposed invention, transducer T is used as a transmitting transducer only. Transducer B operates as a receiving transducer (in a "pitch-catch" mode) following a transmission from Transducer T, and as a transmitting and receiving transducer in a "pulse echo" mode when it generates an ultrasonic pulse that, if the pipe 12 is full, is reflected from the upper interior pipe wall 24, and, if the pipe 12 contains a gas bubble, off the gas-water interface. The transit times for each of these transmissions are measured. If no signal is received by transducer B as a result of the transmission from transducer T, this is taken as an indication of a void formation in the top of the pipe 12 (the void greatly attenuates the acoustic energy from the top transducer that reaches the bottom transducer, thereby preventing the reception of a valid signal). The transit time of the pulse echo transmission from Transducer B is then used to determine the height of the water column as measured from the bottom of the pipe 12. The height measurement is then used to calculate the fraction of the pipe 12 filled with gas. As shown in Table 1 and FIG. 1, a multiplexing arrangement allows the use of a single set of electronics—transmitter, receiver, signal detection, and processing—to detect the presence of voids and to calculate the void fraction in multiple pipes of multiple systems. FIGS. 2a-2c together comprise a flow chart of the measurements and their interpretation for one pipe for the first configuration disclosed herein.

Referring to FIGS. 1 and 3, there is shown the first configuration of an apparatus 10 for detecting and measuring gas voids 22 in a pipe 12 with a fluid (void shown in FIG. 3). The pipe is labeled pipe 1 in FIG. 1 to denote the fact that the invention can monitor several pipes. The apparatus 10 comprises transducer 18 externally disposed on the top of pipe 12 and transducer 20 externally disposed on the bottom of pipe 12, said transducers generating and receiving pulses of ultrasonic energy that characterize the properties of the fluid internal to the pipe 12. The apparatus 10 comprises a transmitter 14 in communication with the transducers 18 and 20 via the switches of a multiplexer 13 which switches are, for pipe 1, 1BT (24) and 1TT (25). A receiver 15 is also part of the apparatus 10 and is in communication with transducer 1B (20), via switch 1BR (23) of the multiplexer 13. Additional switches 26 in multiplexer 13 allow communication between the transmitter 14 and receiver 15 and transducers on other pipes, n in number (there is no specific limit) for applications where the apparatus 10 is used to monitor voids in multiple pipes. A controller 16 is in communication with the multiplexer, 13, and the transmitter 14 and receiver 15, controlling the transmission and reception of ultrasonic signals, verifying the receipt of valid signals (or confirming that no valid signal has been received), and measuring the transit times of the pulses of ultrasound when valid signals are received. Data from the controller 16 are transmitted to the processor 17, which computes the sound velocity of the fluid in the pipe, when valid signals are received, and which computes the height L 27 (FIG. 3) of the liquid in the pipe when no valid signal is received on a transmission from transducer T 18. For this computation the processor 17 uses a fluid sound velocity for the pulse transmission sequence for which the last valid signal transmitted by transducer T 18 was received by transducer B20. From the height of liquid 27 the processor 17 also computes the fraction of the pipe 12 that is filled with gas void.

The controller 16 is in communication with the transmitter 14, the receiver 15 and the multiplexer 13, which connects the appropriate electronic device to the top and bottom transducers on each pipe that is monitored and can cause the first and second transducers to produce and detect ultrasonic transmissions in the sequence described below.

Description of the Sequence for the First Configuration

In following the numbered sequence below, reference should be made to Table 1 which diagrams the operation of the multiplexer (an X in this table means the contact is closed), the block diagram of FIG. 1, and the flow chart of FIGS. 2a-2c.

I. The controller 16 closes contact 1TT 25 of the multiplexer 13 connecting the transmitter 14 to the top transducer 18, and initiates a pulse transmission from the top transducer 18 toward the bottom transducer 20. All other contacts of the multiplexer are open.

II. As is common in most ultrasonic pulse transmission and reception systems, a range gate, located in the controller, is employed to enable the receiver to look for a pulse in the time window in which it is expected. As shown in the flow chart, FIG. 2, range gate RGTB1 is employed for the transmission from the top transducer T1 18 on pipe 1 to the bottom transducer B1 20 on pipe 1. This range gate controls contact 1BR 23 of the multiplexer 13, closing it for the duration of the range gate time window; contact 1BR 23 connects the bottom transducer 20 to the receiver 15. All other contacts of the multiplexer are open. All electrical energy received by the bottom transducer 20 while the range gate is enabled is processed by the receiver 15 and evaluated by the controller 16 to determine whether a valid signal is present. If a valid signal is received, there is no void 22 present; if no valid signal is received while the range gate is enabled, a void 22 is present. If no valid signal has been received by the time the range gate is disabled (contact 1BR 23 opens), the controller transmits this information to the processor in the form of a "flag" (F1 in the flow chart), which provides a "void alert for pipe 1" output. If a valid signal is received during the period when the range gate is enabled, the controller measures the total transit time from the initiation of pulse transmission to the reception of a valid signal. This transit time is transmitted to the processor 17 where it will be used with a second transit time measured in a later sequence for the computation of sound velocity and non fluid delays for pipe 1. The measured transit time is also used to adjust range gate RGTB1 for the next transmission. The adjustment may be necessary because the sound velocity of the fluid in pipe 1 will change if the fluid temperature changes. As shown on the flow chart the range gate RGTB1 is adjusted so that it is enabled (reception allowed), following transmission by an amount 8 µseconds less than the measured transit time (the number is given as an example only). As the Flow Chart also shows the range gate is disabled (reception prevented) 3 µseconds after the measured transit time (again the number is an example only).

III. After the steps outlined in II. are completed, the controller 16 closes contact 1BT 25 connecting the transmitter 14 to the bottom transducer 20, and initiates a pulse transmission which will be either reflected off the interior surface of the upper side of the pipe if the pipe is full of liquid or off the surface of the liquid-void interface, but in either case will be reflected in the direction of the bottom transducer 20. All other contacts of the multiplexer are open.

IV. Following step III, the pulse echo transmission from the bottom transducer 20, the controller 17 uses a second range gate, RGBB1 to control contact 1BR 23 of the multiplexer 13, which contact again connects the bottom transducer 20 to the receiver 15 during the time window in which the pulse is expected to be received. All other multiplexer contacts are open. If a valid signal is received during the period when the range gate is enabled, the controller measures the total transit time from the initiation of pulse transmission to the reception of a valid signal. This transit time is transmitted to the processor 17 where it will be used with the transit time measured in sequence step II for the computation of sound velocity and non fluid delays for pipe 1. The measured transit time is also used to adjust range gate RGBB1 for the next transmission. As shown on the flow chart the range gate RGBB1 is adjusted so that it is enabled (reception allowed), following transmission by an amount 8 µseconds less than the measured transit time (the number is given as an example only). As the flow chart also shows the range gate is disabled (reception prevented) by an amount 3 µseconds greater than the measured transit time (again the number is an example only). Because the transmission of this step from and to transducer B is a pulse echo transmission, a valid signal will be received if there is fluid in the pipe above a detectable minimum. Hence if no signal is received for the duration of the range gate, there is no measurable fluid present, as shown on the flow chart. For both cases—valid signal or no—the information is transmitted from the controller 16 to the processor 17 for appropriate processing and output.

V. If the transmission of step I is successfully received by the bottom transducer in step II and the transmission of step III is successfully received in step IV, the transit times measured steps in steps II and IV can be converted by the processor 17 into a measurement of the non fluid delays for these transmissions and a measurement of fluid sound velocity in pipe 1 (The algorithm is described in a later section). If the transmission of step I from the top transducer 18 is not received by the bottom transducer 20 in step II, the controller 16 sets a flag, as shown in the flow chart, which causes the processor 17 to convert the transit time of the reflected transmission of step III from the bottom transducer 20 and received by the bottom transducer 20 in step IV into a liquid height measurement. The conversion to height by the signal processor 17 can be made using sound velocity and non fluid delay measurements derived from transit times associated with prior transmissions from the top transducer 18 for which a valid signal was received by the bottom transducer 20. When both transmissions are successful, the flow chart shows that N multiple samples of successful transit time measurements can be used to determine the sound velocity and non fluid delays that are used to compute liquid height when the top to bottom transmission is unsuccessful. The use of multiple samples reduces random errors in the sound velocity and non fluid delays due to turbulence and other factors. The required number of samples N is input by the user.

VI. From the liquid height measurement and a pipe internal diameter input by the user, the processor 17 can determine what fraction of the pipe 12 is filled with gas.

VII. Following the completion of measurements for pipe 1, the controller 16 causes the multiplexer 13 to repeat the sequence above for pipe 2, then for pipe 3, and so on until completion of the sequence for the nth pipe, whereupon the sequence is repeated for pipe 1, and so on ad infinitum.

Description of the Sequence for the Second Configuration

Refer to FIG. 5 and Table 2. The arrangement of transducers 18 and 20 is identical to that of the first configuration. The sequence of operation for the second configuration is likewise identical for steps I, II, III, and IV as described above for the first configuration, whether the pipe is full (transmission from the top transducer 18 is successfully received by the bottom transducer 20) or if a void is present (transmission from the top transducer 18 not received by the bottom transducer 20). In the second configuration additional transmissions are employed, as described by the sequence below, which starts after completion of step IV. Steps V, VI, VII, and VIII are taken only if a valid pulse is received in step II. If no valid pulse is received in step II, the sequence proceeds directly to step IX below.

V If a valid pulse has been received in II, the controller 16 closes contact 1BT 25 connecting the transmitter 14 to the bottom transducer 20, and transmits a pulse which will be received by the top transducer 18 (since the pipe is full). All other contacts of the multiplexer are open.

VI A range gate RGBT1 (This sequence is not shown on the flow chart of FIG. 2, which applies to the first configuration) causes the controller 16 to close contact 1TR 30 for the period during which a pulse transmitted from the bottom transducer is expected to arrive at the top transducer, plus or minus a tolerance. All other multiplexer contacts are open. When a valid signal is received during the period when the range gate is enabled, the controller 16 measures the total transit time, from the initiation of pulse transmission to the reception of a valid signal. This transit time is transmitted to the processor 17 where it will be used with other measured transit times for the computation of sound velocity and non fluid delays for pipe 1. The measured transit time is also used to adjust range gate RGBT1 for the next transmission.

VII If a valid pulse has been received in II and following step VI, the controller 16 closes contact 1TT 25 connecting the transmitter 14 to the top transducer 18, and transmits a pulse which, after reflection from the bottom interior surface of the pipe, will be received by the top transducer 18 (since the pipe is full). All other multiplexer contacts are open.

VIII A range gate RGTT1 (This sequence is not shown on the flow chart of FIG. 2) causes the controller 16 to close contact 1TR 30 for the period (plus or minus a tolerance) during which a pulse transmitted from the top transducer 18 is expected to arrive at the top transducer 18, having being reflected by the bottom interior surface of the pipe. All other multiplexer contacts are open. When a valid signal is received during the period when the range gate is enabled, the controller measures the total transit time from the initiation of pulse transmission to the reception of a valid signal. This transit time is transmitted to the processor 17 where it will be used with other measured transit times for the computation of sound velocity and non fluid delays for pipe 1. The measured transit time is also used to adjust range gate RGTT1 for the next transmission.

IX If the transmission of step I is successfully received by the bottom transducer in step II, the transit times measured steps in steps II, IV, VI, and VIII can be converted by the processor 17 into a measurement of the non fluid delays for these transmissions and a measurement of the sound velocity of the fluid in pipe 1 (The algorithm is described in a later section). If the transmission of step I from the top transducer 18 is not received by the bottom transducer 20 in step II, the controller 16 sets a flag, as shown in the flow chart for the sequence of the first configuration, which causes the processor 17 to convert the transit time of the reflected transmission of step III from the bottom transducer 20 and received by the bottom transducer 20 in step IV into a liquid height measurement. Also when no valid signal is received in step II, the transmissions of steps V and VII are halted. The conversion to height by the signal processor 17 can be made using sound velocity and non fluid delay measurements derived from transit times associated with all transmissions prior to the failure of a valid signal from the top transducer 18 to reach the bottom transducer 20. When all transmissions are successful, the transit time measurements can be used to determine the sound velocity and non fluid delays that are used to compute liquid height when the top to bottom transmission is unsuccessful.

X From the liquid height measurement and a pipe internal diameter input by the user, the processor 17 can determine what fraction of the pipe 12 is filled with gas.

XI Following the completion of measurements for pipe 1, the controller 16 causes the multiplexer 13 to repeat the sequence above for pipe 2, then for pipe 3, and so on until completion of the sequence for the nth pipe, whereupon the sequence is repeated for pipe 1, and so on ad infinitum.

Description of the Algorithm

If the pipe 12 is full, the transit time from initiation of transmission by transducer T to the detection of a received signal by transducer B is given by $$t_{TB} = \tau_{Tt} + \tau_{Br} + ID/C \qquad 1)$$

$t_{TB}$ Time of flight for an ultrasonic pulse traveling from transducer T to transducer B if the pipe 12 is full. The time includes the transit time through to column of liquid separating the interior of the pipe 12 at T and the interior of the pipe 12 at B as well as the electronic and acoustic delays of the non fluid media between the transmitter and the signal detection electronics.

$\tau_{Tr}$ The non fluid delay associated with transmission from transducer T: the transmitter delay, the transit time for the cable from the transmitter to the transducer T, the delay of transducer T, the transit time through the pipe wall at T, $\tau_{Br}$ The transit time through the pipe wall at B, the delay of transducer B, the transit time for the cable from transducer B to the receiver, the delay of the receiver electronics, and the delay associated with pulse detection and transit time measurement (for example, if the zero crossing of the second half cycle of the received signal is used for the transit time measurement, the delay associated with the first cycle of the received signal).

ID The internal diameter of the pipe 12 (entered by the user).

C The velocity of sound in the fluid contained by the pipe 12. Transverse fluid velocity components owing to natural convection are 3 orders of magnitude less than the sound velocity and are therefore negligible.

If the pipe 12 is not full, a gas bubble will blanket the pipe wall immediately below transducer T and will prevent the transmission of ultrasound to transducer B.

If the pipe 12 is full, the transit time of ultrasound from the initiation of transmission from Transducer B, operating in a pulse-echo mode, to its reception and detection by the same transducer is given by:

$$2t_{BB} = \tau_{Bt} + \tau_{Br} + 2ID/C \qquad 2)$$

$t_{BB}$ is the transit time, from transmission to detection, of ultrasound traveling from transducer B, reflected off the upper wall of the pipe 12 and received by transducer B.

$\tau_{Bt}$ The non fluid delay associated with transmission from transducer B: the transmitter delay, the transit time for the cable from the transmitter to the transducer B, the delay of transducer B, the transit time through the pipe wall at B.

In the first configuration or mode of operation, it is assumed that $\tau_{Bt}$, the non fluid delay associated with transmission from transducer B is essentially the same as to $\tau_{Tt}$, the non fluid delay associated with transmission from transducer T: The same transmitter is used for both transmissions, the cable lengths can be made the same, the transducers are of the same configuration, and the pipe wall thicknesses at the T and B locations are within a few per cent of each other. Therefore, $\tau_{Bt} + \tau_{Br}$ can be substituted for $\tau_{Tt} + \tau_{Br}$ in equation (1). Making this substitution and subtracting equation (1) from equation (2), an expression is obtained for the velocity of sound.

$$ID/C \cong t_{BB} - t_{TB} \qquad 3)$$

$$C \cong ID/(t_{BB} - t_{TB}) \qquad 3A)$$

When the pipe 12 is full, the expression of (3A) can be used to in the formation of a rolling average of the sound velocity of the fluid in the pipe 12, as shown in the flow chart of FIG. 2 (sound velocity will change if the temperature of the fluid changes). A rolling average may not be necessary if temperature varies slowly. The flow chart is intended to show how a rolling average would be formed if it is found necessary. As the flow chart also shows, if a void 22 begins to form, the average sound velocity that was computed while the pipe 12 was full is used, along with the average of the non fluid delays measured when the pipe was full, to find the level of the water in the pipe. The process of determining the non fluid delays is described in the paragraphs following.

The total non fluid delays associated with operating transducer B in the pulse-echo mode, $\tau_{Bt} + \tau_{Br}$, are found by substituting equation (3) in equation (2).

$$t_{BB} \cong \tau_{Bt} + \tau_{Br} + 2(t_{BB} - t_{TB}) \qquad 4)$$

$$\tau_{Bt} + \tau_{Br} \cong 2 t_{TB} - t_{BB} \qquad 4A)$$

Again, as shown in the flow chart of FIG. 2, a rolling average of the total pulse echo non fluid delay is compiled while the pipe 12 is full, for use after a void 22 begins to form. Again, a rolling average may not be necessary for the computation of the delays, but is shown for completeness.

If a void 22 begins to form, as evidenced by a failure to receive a signal on the transmission from transducer T to transducer B, the transit time of the pulse-echo transmission from transducer B is used to determine the water level L in the pipe 12:

$$t_{BB} \cong (\tau_{Bt} + \tau_{Br})_0 + 2L/C_0 \qquad 5)$$

$$L \cong [t_{BB} - (\tau_{Bt} + \tau_{Br})_0] C_0/2 \qquad 5A)$$

Here, $(\tau_{Bt} + \tau_{Br})_0$ and $C_0$ are, respectively, the rolling average non fluid delays and fluid sound velocity compiled while pipe 12 was full. The approximation sign in (5) and (5A) is intended to convey the uncertainties in the assumption that $\tau_{Tt}$ is equal to $\tau_{Bt}$.

The second configuration or mode of operation is shown in FIG. 5. Multiplexer operation is described in Table 2. No flow chart is provided; the logic is generally similar to that of Mode A, except as necessary to accommodate 4 transmissions. When the pipe is full, the second configuration utilizes four transmissions as follows:

(a) A pitch catch transmission from T to B, identical to that of mode 1. For this transmission, the transit time, $t_{TB}$ expressed in equation (1) and repeated below, is measured $$t_{TB} = \tau_{Tt} + \tau_{Br} + ID/C \qquad 1)$$

(b) A pulse echo transmission from B to B. also identical to that of mode 1. For this transmission, the transit time, $t_{BB}$ expressed in equation (2) and repeated below, is measured $$t_{BB} = \tau_{Bt} + \tau_{Br} + 2 ID/C \qquad 2)$$

(c) A pitch catch transmission from B to T For this transmission, the transit time, $t_{BT}$ expressed in equation (6) below, is measured. This transmission is initiated only when the pipe is full, as evidenced by a successful transmission from T to B.

$$t_{BT} = \tau_{Bt} + \tau_{Tr} + ID/C \qquad 6)$$

(d) A pulse echo transmission from T to T For this transmission, the transit time, $t_{TT}$ expressed in equation (7) below, is measured. Again, this transmission is initiated only when the pipe is full, as evidenced by a successful transmission from T to B.

$$t_{TT} = \tau_{Tt} + \tau_{Tr} + 2 ID/C \qquad 7)$$

The four equations above (1), (2), (6) and (7) can be solved with no approximations for the non fluid delays $\tau_{Bt}$ and $\tau_{Br}$, the delays necessary to find the level of fluid L in equation 5A. Specifically it can be shown that:

$$\tau_{Bt}+\tau_{Br}=t_{TT}-t_{TB}-t_{BT} \quad (8)$$

The equations can also be used to find the sound velocity without the delay approximation:

$$C=2\ ID/(t_{BB}+t_{TT}-t_{TB}-t_{BT}) \quad (9)$$

As noted above, when a void begins to form in the pipe, as evidenced by the failure to receive a transmission from T at B, the pulse-echo transmission from T to T is halted, as is the pitch catch transmission from B to T. In a partly full pipe these transmissions serve no useful purpose. The T to T and B to T transmissions are resumed only when the pipe is refilled and successful T to B transmissions resume.

Both configurations of the disclosed invention employ the same algorithm for the conversion of water level height L to void area fraction. Refer to FIG. 3. Given a water level L, the void area $A_{VOID}$ is given by (Eshbach, *Handbook of Engineering Fundamentals*, Section 2, Table 1b, incorporated by reference, herein):

$$A_{VOID}=ID^2/8\ [2\phi-\sin(2\phi)] \quad (6)$$

The void area fraction, VF is obtained by dividing equation (6) by the pipe area, $\pi\ ID^2/4$:

$$VF=1/(2\pi)\times[2\phi-\sin(2\phi)] \quad (6A)$$

The angle $\phi$ is given by:

$$\phi=\arccos(2L/ID-1) \quad (7)$$

Figure 4:
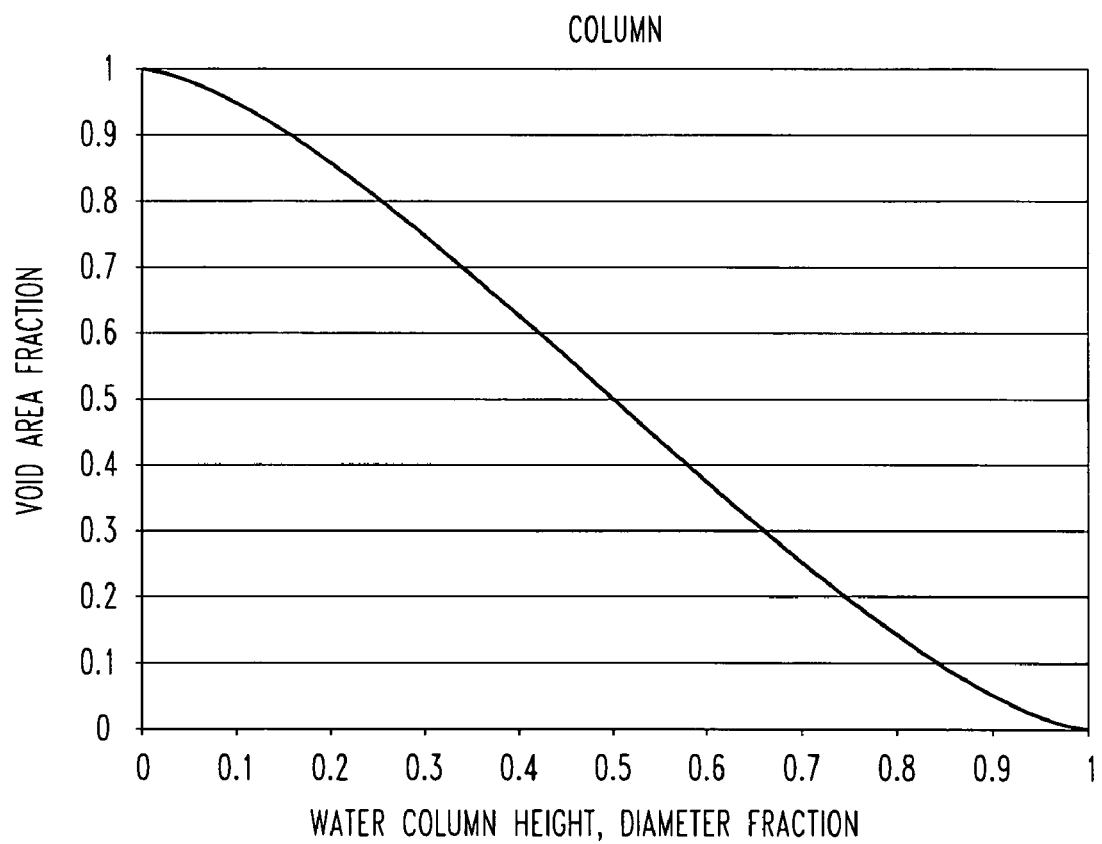
FIG. 4 is a graph of void fraction as a function of level normalized to the pipe internal diameter.

FIG. 4 is a plot of the void fraction as a function of level, normalized to the pipe internal diameter.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for detecting and measuring gas voids in a pipe with a fluid comprising:
   a first ultrasonic transducer externally disposed on the pipe;
   a second ultrasonic transducer externally disposed on the pipe; and
   a multiplexer, transmitter, receiver, controller and processor in communication with the first transducer and the second transducer which in combination identify a void in the pipe from ultrasonic measurements of properties of the fluid in the pipe from the first and second ultrasonic transducers and wherein the first ultrasonic transducer is disposed externally on the top of the pipe, and the second ultrasonic transducer is disposed externally on the bottom of the pipe essentially below the first transducer so a diametrical path by the ultrasonic energy is followed between the first and second transducers.

2. The apparatus as described in claim 1 including a controller; a multiplexer; a transmitter and a receiver in communication via the multiplexer with the first and second transducers which causes the first and second transducers to produce ultrasonic transmissions to occur sequentially as follows:
   a transmission from the first transducer to the second transducer; if the transmission is received by second trans-

TABLE 1

Truth Table, Multiplexer Transmit and Receive Control, First Configuration

| Pipe | Operation | 1BR | 1BT | 1TT | 2BR | 2BT | 2TT | nBR | nBT | nTT |
|---|---|---|---|---|---|---|---|---|---|---|
| Pipe 1 | Transmit $t_{TB}$ | | | X | | | | | | |
| Pipe 1 | Receive $t_{TB}$ | X | | | | | | | | |
| Pipe 1 | Transmit $t_{BB}$ | | X | | | | | | | |
| Pipe 1 | Receive $t_{BB}$ | X | | | | | | | | |
| Pipe 2 | Transmit $t_{TB}$ | | | | | | X | | | |
| Pipe 2 | Receive $t_{TB}$ | | | | X | | | | | |
| Pipe 2 | Transmit $t_{BB}$ | | | | | X | | | | |
| Pipe 2 | Receive $t_{BB}$ | | | | X | | | | | |
| Pipe n | Transmit $t_{TB}$ | | | | | | | | | X |
| Pipe n | Receive $t_{TB}$ | | | | | | | X | | |
| Pipe n | Transmit $t_{BB}$ | | | | | | | | X | |
| Pipe n | Receive $t_{BB}$ | | | | | | | X | | |

TABLE 2

Truth Table, Multiplexer Transmit and Receive Control, Second Configuration

| Pipe | Operation | 1BR | 1BT | 1TT | 1TR | nBR | nBT | nTT | nTR |
|---|---|---|---|---|---|---|---|---|---|
| Pipe 1 | Transmit $t_{TB}$ | | | X | | | | | |
| Pipe 1 | Receive $t_{TB}$ | X | | | | | | | |
| Pipe 1 | Transmit $t_{BB}$ | | X | | | | | | |
| Pipe 1 | Receive $t_{BB}$ | X | | | | | | | |
| Pipe 1 | Transmit $t_{BT}$ | | X | | | | | | |
| Pipe 1 | Receive $t_{BT}$ | | | | X | | | | |
| Pipe 1 | Transmit $t_{TT}$ | | | X | | | | | |
| Pipe 1 | Receive $t_{TT}$ | | | | X | | | | |
| Pipe n | Transmit $t_{TB}$ | | | | | | | X | |
| Pipe n | Other transmissions and receptions | | | | | Pattern similar to pipe 1 | | | | ducer as sensed by the receiver and the controller, there is no void present; if the transmission by the first transducer is not received by second transducer, a void is present; and a transmission from the second transducer that is reflected either off the pipe's upper wall, if no void is present, or off the liquid surface, if a void is present.

3. The apparatus as described in claim 2 wherein if the transmission from the first transducer is received by the second transducer, transit times from this transmission and from a transmission from the second transducer to itself via a reflection are converted by the processor into a fluid sound velocity measurement, if the transmission from the first transducer is not received by the second transducer, a transit time of the transmission from the second transducer to itself is converted by the processor into a liquid height measurement.

4. The apparatus as described in claim 2 wherein if the transmission from the first transducer is received by the second transducer, transit times from this transmission and from a transmission from the second transducer to itself via a reflection are converted by the processor into a measurement of the non fluid time delays associated with the second transmission; said non fluid delays also being used, if the transmission from the first transducer is not received by the second transducer, for the conversion by the processor of the transit time of the second transducer to itself into a liquid height measurement.

5. The apparatus as described in claim 4 wherein the conversion to height by the processor is made using a fluid sound velocity measurement and non fluid delay measurement associated with the last transmission from the first transducer that was received by the second transducer.

6. The apparatus as described in claim 5 wherein the processor determines what fraction of the pipe is filled with gas.

7. The apparatus as described in claim 6 wherein the signal from the first transducer follows a diametric path through the pipe wall, the interior of the pipe and the pipe wall to the second transducer if there is no void.

8. The apparatus as described in claim 7 wherein the multiplexer, transmitter, receiver, controller and processor process transmissions to detect and measure voids from additional transducers disposed on other pipes.

9. The apparatus as described in claim 8 wherein the processor issues an alert for the pipe when a threshold associated with a void in the pipe is reached.

10. The apparatus as described in claim 9 wherein a transmission from the second transducer follows and retraces a diametric path through the pipe and the interior of the pipe if there is no void, and a path that lies along the diameter but is a fraction thereof if there is a void.

11. The apparatus as described in claim 1 wherein the controller causes the first and second transducers to produce ultrasonic transmissions to occur sequentially as follows:

a first transmission from the first transducer to the second transducer; if the transmission is received by second transducer as sensed by the receiver and the controller, there is no void present; if the first transmission by the first transducer is not received by the second transducer, a void is present;

a second transmission from the second transducer that is reflected either off the pipe's upper wall, if no void is present, or off the liquid surface, if a void is present, returning to the second transducer;

if the first transmission from the first transducer is received by the second transducer, a third transmission from the bottom transducer to the top transducer, and if the first transmission from the first transducer is received by the second transducer, a transmission from the first transducer to the first transducer, by way of a reflection from the bottom of the pipe.

12. The apparatus as described in claim 11 wherein if the first transmission from the first transducer is received by the second transducer, transit times from the first transmission and from the second, third and fourth transmissions are converted by the processor into a fluid sound velocity measurement; if the first transmission from the first transducer is not received by the second transducer, the transit time of the second transmission from the second transducer to itself is converted by the processor into a liquid height measurement.

13. The apparatus as described in claim 12 wherein if the first transmission from the first transducer is received by the second transducer, transit times from the first transmission and from the second, third and fourth transmissions are converted by the processor into a measurement of non fluid time delays associated with the second transmission, said non fluid delays also being used, by the processor, if the first transmission from the first transducer is not received by the second transducer, for the conversion of the transit time of the second transducer to itself into a liquid height measurement.

14. The apparatus as described in claim 13 wherein the conversion to height by the processor is made using a fluid sound velocity measurement and non fluid delay measurement associated with a last transmission from the first transducer that was received by the second transducer.

15. A method for detecting and measuring gas voids in a pipe with a fluid comprising the steps of:

measuring properties of the fluid internal to the pipe with transmissions of ultrasonic energy from transducers externally disposed on the pipe; and identifying a void in the pipe from the properties of the fluid internal to the pipe using signals associated with the ultrasonic energy processed by a processor and disposing a first transducer externally on the top of the pipe and a second ultrasonic transducer externally on the bottom of the pipe essentially below the first transducer wherein a diametrical path by the ultrasonic energy is followed between the first and second transducers.

16. A method as described in claim 15 including the step of causing with a multiplexer and a controller a first ultrasonic transducer disposed externally on the top of the pipe and a second ultrasonic transducer disposed externally on the bottom of the pipe essentially below the first transducer to produce ultrasonic transmissions to occur sequentially as follows:

a transmission from the first transducer to the second transducer; if the transmission is received by second transducer as sensed by the receiver and the controller, there is no void present; if the transmission by the first transducer is not received by second transducer, a void is present; and a transmission from the second transducer that is reflected either off the pipe's upper wall, if no void is present or off the liquid surface if a void is present, returning to the second transducer.

17. The method as described in claim 16 wherein if the transmission from the first transducer is received by the second transducer, there is a step of converting transit times from the transmission and from a transmission from the second transducer to itself via a reflection by a processor into a fluid sound velocity measurement, if the transmission from the first transducer is not received by the second transducer, there is the step of converting a transit time of the transmission from the second transducer to itself by the processor into a liquid height measurement.

18. The method as described in claim 17 wherein the step of converting to height by the processor includes the step of converting to height using a fluid sound velocity measurement and a non fluid delay measurement associated with the last transmission from the first transducer for which the last transmission was received by the second transducer.

19. The method as described in claim 18 including the step of determining with the processor what fraction of the pipe is filled with gas.

20. The method as described in claim 19 wherein the signal from the first transducer follows a diametric path through the pipe wall, the interior of the pipe and the pipe wall to the second transducer if there is no void.

21. The method as described in claim 20 including the step of processing with the multiplexer, transmitter, receiver, controller and a processor transmissions to detect and measure voids from additional transducers disposed on other pipes.

22. The apparatus as described in claim 21 including the step of issuing an alert by the processor when a threshold associated with a void in the pipe is reached.

23. The method as described in claim 22 wherein a transmission from the second transducer follows and retraces a diametric path through the pipe and the interior of the pipe if there is no void, and a path that lies along the diameter but is a fraction thereof if there is a void.

\* \* \* \* \*